US012583809B2

(12) United States Patent
Birkbeck et al.

(10) Patent No.: US 12,583,809 B2
(45) Date of Patent: Mar. 24, 2026

(54) PROCESS FOR PREPARING INDENE ACRYLADEHYDE DERIVATIVES

(71) Applicant: Firmenich SA, Satigny (CH)

(72) Inventors: Anthony Alexander Birkbeck, Satigny (CH); Atulkumar Manvar, Bharuch (IN); Eric Walther, Satigny (CH)

(73) Assignee: FIRMENICH SA, Satigny (CH)

( * ) Notice: Subject to any disclaimer, the term of this patent is extended or adjusted under 35 U.S.C. 154(b) by 538 days.

(21) Appl. No.: 18/006,721

(22) PCT Filed: Jul. 20, 2021

(86) PCT No.: PCT/EP2021/070208

§ 371 (c)(1),
(2) Date: Jan. 24, 2023

(87) PCT Pub. No.: WO2022/018054

PCT Pub. Date: Jan. 27, 2022

(65) Prior Publication Data

US 2023/0271911 A1 Aug. 31, 2023

(30) Foreign Application Priority Data

Jul. 24, 2020 (IN) ............................ 202011031857
Sep. 7, 2020 (EP) .................................... 20194753

(51) Int. Cl.

| | |
|---|---|
| ***C07C 47/238*** | (2006.01) |
| ***C07C 41/56*** | (2006.01) |
| ***C07C 43/303*** | (2006.01) |
| ***C07C 43/307*** | (2006.01) |
| ***C07C 45/29*** | (2006.01) |

(52) U.S. Cl.

CPC ............ *C07C 47/238* (2013.01); *C07C 41/56* (2013.01); *C07C 43/303* (2013.01); *C07C 43/307* (2013.01); *C07C 45/29* (2013.01); *C07C 2602/08* (2017.05)

(58) Field of Classification Search

USPC .......................................................... 568/433
See application file for complete search history.

(56) References Cited

U.S. PATENT DOCUMENTS 2,165,962 A 7/1939 Pieroh et al.
5,084,440 A 1/1992 Baudin et al.

FOREIGN PATENT DOCUMENTS

EP 0 685 444 A1 12/1995
WO 2006/120639 A2 11/2006
WO 2017/066214 A1 4/2017

OTHER PUBLICATIONS

"Utilization of p-Cymene in the Synthesis of Perfume Compounds. V. Synthesis of Some Derivatives of 1,1,3,3,5-Pentamethylindan", Przemysl Chemiczny, 1996, pp. 570-571, 45(10).
Nätscher et al., "Lower Homologues of Okoumal and Disila-Okoumal: Synthesis and Olfactory Characterization of Novel Ambergris Odorants", ChemBioChem, 2010, pp. 315-319, 11(3).
CAS registry No. 883836-77-9, SciFinder, 2025, pp. 1-2.
CAS registry No. 1267875-99-9, SciFinder, 2025, pp. 1-2.
CAS registry No. 1268101-47-8, SciFinder, 2025, pp. 1-2.

*Primary Examiner* — Ana Z Muresan
(74) *Attorney, Agent, or Firm* — Armstrong Teasdale LLP

(57) ABSTRACT

The present invention relates to the field of perfumery. More particularly, it concerns valuable new chemical intermediates for producing perfuming ingredients. Moreover, the present invention also comprises a process for producing compound of formula (I).

(I)

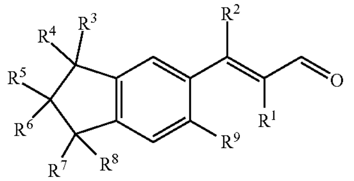

16 Claims, No Drawings

PROCESS FOR PREPARING INDENE ACRYLADEHYDE DERIVATIVES

This present application is a U.S. national phase entry under 35 U.S.C. § 371 of PCT Application No. PCT/EP2021/070208, filed Jul. 20, 2021, which claims priority to Indian Patent Application number 202011031857, filed Jul. 24, 2020 and European Patent Application No. 20194753.8, filed Sep. 7, 2020. The entire contents of these applications are explicitly incorporated herein by this reference.

TECHNICAL FIELD

The present invention relates to the field of perfumery. More particularly, it concerns valuable new chemical intermediates for producing perfuming ingredients. Moreover, the present invention also comprises of a process for producing compounds of formula (I).

BACKGROUND OF THE INVENTION

In the perfumery industry, there is a constant need to provide compounds imparting novel organoleptic notes. In particular, there is an interest towards ingredients imparting the lily of the valley odor or at least one of the key organoleptic facets of the lily of the valley odor. So, compounds imparting said note are particularly sought after to reconstitute the delicate floral odor of muguet which does not survive even the mildest of extraction methods to yield an essential oil. Towards this goal, compounds of formula (V) were previously reported in EP 685444, and in particular 2,3-dihydro-1,1-dimethyl-1H-Indene-ar-propanal also known as Hivernal® (origin: Firmenich SA) which were obtained via the condensation between the 2,3-dihydro-1H-indene derivative and an unsaturated diacetate in the presence of $TiCl_4$. Catalytic conditions have been developed as disclosed in WO2006120639. However, the reported route to obtain compounds of formula (I) suffers from the generation of chlorinated waste and also from the generation of a complex mixture of isomers. In addition, being products of industrial interest, there is always a need for new processes showing improved yields and increased conversions.

So, there is a need to develop an approach toward compounds of formula (V) using reagents which may be safer while limiting the formation of isomers.

The present invention is a process for obtaining compound of formula (V) starting from compound of formula (II) due to a novel route through novel intermediates, never disclosed before, while controlling the isomers formed. In particular, the compounds of formula (III) and (IV) which are an object of the present invention, have never been reported or suggested in the context of the preparation of compounds of formula (V). Whilst a few of said compounds of formula (III) are known and have been previously reported in the prior art, none of these compounds have been used as intermediates in the synthesis of compounds of formula (V). reporting some derivatives of formula (III) cannot be considered as suggesting the present invention.

SUMMARY OF THE INVENTION

The invention relates to a novel process allowing the preparation of compound of formula (I) starting from compound of formula (II) opening a new route towards compounds of formula (V).

So, the first object of the present invention is a process for the preparation of a compound of formula (I)

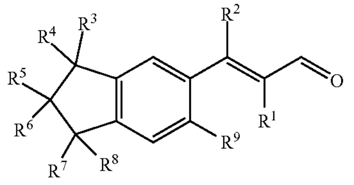

in the form of any one of their stereoisomers or a mixture thereof, and wherein $R^1$ and $R^2$, independently from each other, represent a hydrogen atom or a $C_{1-2}$ alkyl group; $R^9$ represents a hydrogen atom or a methyl group; $R^3$, $R^4$, $R^5$, $R^6$, $R^7$ and $R^8$, independently from each other, represent a hydrogen atom or a $C_{1-4}$ alkyl group; or two groups among $R^3$, $R^4$, $R^5$, $R^6$, $R^7$ and $R^8$ are taken together and form a $C_{3-8}$ cycloalkyl or $C_{5-8}$ cycloalkenyl group and the others groups have the same meaning as defined above;

comprising the steps of a) converting a compound of formula (II)

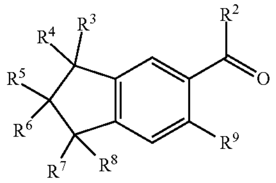

in the form of any one of their stereoisomers or a mixture thereof, and wherein $R^2$, $R^3$, $R^4$, $R^5$, $R^6$, $R^7$, $R^8$ and $R^9$ have the same meaning as defined above;

into an acetal of formula (III)

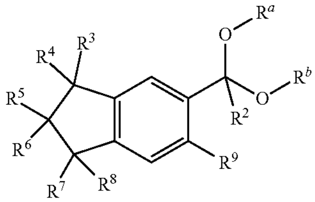

in the form of any one of their stereoisomers or a mixture thereof, and wherein $R^2$, $R^3$, $R^4$, $R^5$, $R^6$, $R^7$, $R^8$ and $R^9$ have the same meaning as defined above; $R^a$ and $R^b$, independently from each other, represent a $C_{1-4}$ alkyl group or $R^a$ and $R^b$, when taken together, represent a $C_{2-5}$ alkanediyl group;

b) treating the acetal obtained in step a) with an acid and a compound of formula $CHR^1{=}CH{-}OR^c$; wherein $R^c$ represents a $C_{1-4}$ alkyl group and $R^1$ has the same meaning as defined above; to obtain a compound of formula (IV)

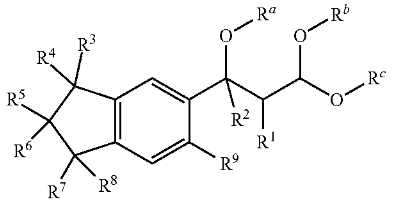

in the form of any one of their stereoisomers or a mixture thereof, and wherein $R^1$, $R^2$, $R^3$, $R^4$, $R^5$, $R^6$, $R^7$, $R^8$, $R^9$, $R^a$, $R^b$ and $R^c$ have the same meaning as defined above; and c) treating the compound of formula (IV) with an acid to obtain a compound of formula (I).

A second object of the present invention is a compound of formula (III)

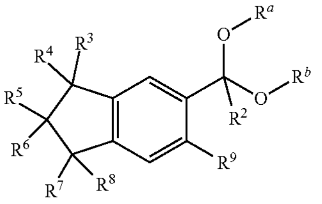

in the form of any one of their stereoisomers or a mixture thereof, and wherein $R^2$ represents a hydrogen atom or a $C_{1-2}$ alkyl group $R^3$, $R^4$, $R^5$, $R^6$, $R^7$ and $R^8$, independently from each other, represent a hydrogen atom or a $C_{1-4}$ alkyl group; or two groups among $R^3$, $R^4$, $R^5$, $R^6$, $R^7$ and $R^8$ are taken together and form a $C_{3-8}$ cycloalkyl or $C_{5-8}$ cycloalkenyl group and the others groups have the same meaning as defined above; $R^9$ represents a hydrogen atom or a methyl group; $R^a$ and $R^b$, independently from each other, represent a $C_{1-4}$ alkyl group or $R^a$ and $R^b$, when taken together, represent a $C_{2-5}$ alkanediyl group; provided that when $R^a$ and $R^b$ are ethyl groups, then $R^3$, $R^4$, $R^5$, $R^6$, $R^7$ and $R^8$ are not hydrogen atoms and when $R^a$ and $R^b$ are methyl or ethyl groups or $R^a$ and $R^b$ are taken together and represent a 1,2-ethandiyl group, then $R^3$, $R^4$, $R^5$, $R^7$ and $R^8$ being methyl groups and $R^6$ being a hydrogen atom or $R^3$, $R^4$ and $R^8$ being methyl groups, $R^7$ being a ethyl group and $R^5$ and $R^6$ being hydrogens atom are excluded.

A third object of the present invention is a compound of formula (IV)

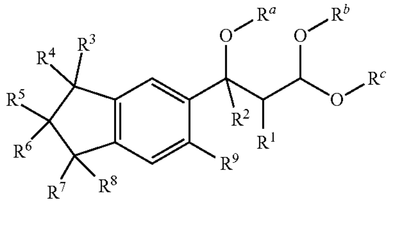

in the form of any one of their stereoisomers or a mixture thereof, and wherein $R^1$ and $R^2$, independently from each other, represent a hydrogen atom or a $C_{1-2}$ alkyl group, $R^3$, $R^4$, $R^5$, $R^6$, $R^7$ and $R^8$, independently from each other, represent a hydrogen atom or a $C_{1-4}$ alkyl group; or two groups among $R^3$, $R^4$, $R^5$, $R^6$, $R^7$ and $R^8$ are taken together and form a $C_{3-8}$ cycloalkyl or $C_{5-8}$ cycloalkenyl group and the others groups have the same meaning as defined above; $R^9$ represents a hydrogen atom or a methyl group; $R^a$ and $R^b$, independently from each other, represent a $C_{1-4}$ alkyl group or $R^a$ and $R^b$, when taken together, represent a $C_{2-5}$ alkanediyl group; $R^c$ represents a $C_{1-4}$ alkyl group.

A further object of the present invention is a compound of formula (V)

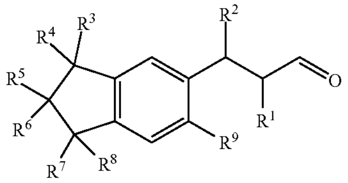

in the form of any one of their stereoisomers or a mixture thereof, and wherein $R^1$ and $R^2$, independently from each other, represent a hydrogen atom or a $C_{1-2}$ alkyl group; $R^9$ represents a hydrogen atom or a methyl group; $R^3$, $R^4$, $R^5$, $R^6$, $R^7$ and $R^8$, independently from each other, represent a hydrogen atom or a $C_{1-4}$ alkyl group; or two groups among $R^3$, $R^4$, $R^5$, $R^6$, $R^7$ and $R^8$ are taken together and form a $C_{3-8}$ cycloalkyl or $C_{5-8}$ cycloalkenyl group and the others groups have the same meaning as defined above;

provided that when $R^9$ is a hydrogen atom, at least one group among $R^3$, $R^4$, $R^5$, $R^6$, $R^7$ and $R^8$, is a $C_{1-4}$ alkyl group; or when $R^9$ is a hydrogen atom and $R^5$ is a methyl or a n-propyl group, at least one group among $R^1$, $R^3$, $R^4$, $R^6$, $R^7$ and $R^8$, is not a hydrogen atom; or 3-(3-methyl-2,3-dihydro-1H-inden-5-yl)propanal, 3-(3-methyl-2,3-dihydro-1H-inden-5-yl)butanal, 3-(1,1-dimethyl-2,3-dihydro-1H-inden-5-yl)propanal, 3-(1,1-dimethyl-2,3-dihydro-1H-inden-5-yl)-2-methylpropanal, 3-(3,3-dimethyl-2,3-dihydro-1H-inden-5-yl)propanal, 3-(3,3-dimethyl-2,3-dihydro-1H-inden-5-yl)-2-methylpropanal or 3-(1,1,6-trimethyl-2,3-dihydro-1H-inden-5-yl)propanal are excluded.

DESCRIPTION OF THE INVENTION

It has now been surprisingly found that the perfuming ingredients reported in EP 685444 can be obtained from a new class of precursors (or chemical intermediates), as defined herein below in formula (III) and (IV), and that said new intermediates allow the corresponding perfuming ingredients to be obtained with overall higher yield, compared to the methods known from the prior art and with less complex isomeric mixtures.

So, the first object of the invention is process for the preparation of a compound of formula (I)

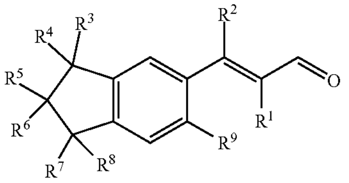

in the form of any one of their stereoisomers or a mixture thereof, and wherein $R^1$ and $R^2$, independently from each other, represent a hydrogen atom or a $C_{1-2}$ alkyl group; $R^9$ represents a hydrogen atom or a methyl group; $R^3$, $R^4$, $R^5$, $R^6$, $R^7$ and $R^8$, independently from each other, represent a hydrogen atom or a $C_{1-4}$ alkyl group; or two groups among $R^3$, $R^4$, $R^5$, $R^6$, $R^7$ and $R^8$ are taken together and form a $C_{3-8}$ cycloalkyl or $C_{5-8}$ cycloalkenyl group and the others groups have the same meaning as defined above;

comprising the steps of a) converting a compound of formula (II)

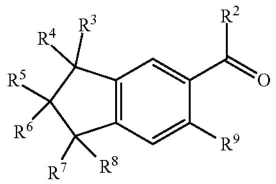

in the form of any one of their stereoisomers or a mixture thereof, and wherein $R^2$, $R^3$, $R^4$, $R^5$, $R^6$, $R^7$, $R^8$ and $R^9$ have the same meaning as defined above;

into an acetal of formula (III)

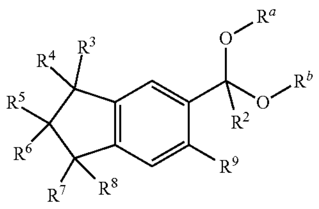

in the form of any one of their stereoisomers or a mixture thereof, and wherein $R^2$, $R^3$, $R^4$, $R^5$, $R^6$, $R^7$, $R^8$ and $R^9$ have the same meaning as defined above; $R^a$ and $R^b$, independently from each other, represent a $C_{1-4}$ alkyl group or $R^a$ and $R^b$, when taken together, represent a $C_{2-5}$ alkanediyl group;

b) treating the acetal obtained in step a) with an acid and a compound of formula $CHR^1{=}CH{-}OR^c$; wherein $R^c$ represents a $C_{1-4}$ alkyl group; to obtain a compound of formula (IV)

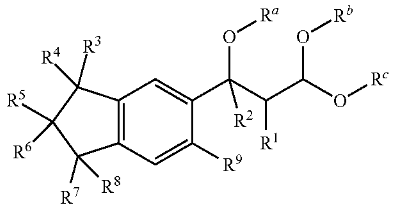

in the form of any one of their stereoisomers or a mixture thereof, and wherein $R^1$, $R^2$, $R^3$, $R^4$, $R^5$, $R^6$, $R^7$, $R^8$, $R^9$, $R^a$, $R^b$ and $R^c$ have the same meaning as defined above; and c) treating the compound of formula (IV) with an acid to obtain a compound of formula (I).

For the sake of clarity, by the expression "any one of its stereoisomers or a mixture thereof", or the similar, it is meant the normal meaning understood by a person skilled in the art, i.e. that the compounds of formula (I), (II), (III) and (IV) can be a pure enantiomer or a mixture of enantiomers. In other words, the compounds of formula (I), (II), (III) and (IV) may possess at least one stereocenter which can have two different stereochemistries (e.g. R or S). The compounds of formula (I), (II), (III) and (IV) may even be in the form of a pure enantiomer or in the form of a mixture of enantiomers. The compounds of formula (I), (II), (III) and (IV) may even be in the form of a pure diastereoisomer or in the form of a mixture of diastereoisomer when compounds of formula (I), (II), (III) and (IV) possess more than one stereocenter. The compounds of formula (I), (II), (III) and (IV) can be in a racemic form or scalemic form. Therefore, the compounds of formula (I), (II), (III) and (IV) can be one stereoisomer or in the form of a composition of matter comprising, or consisting of, various stereoisomers.

According to any one of the above embodiments of the invention, the compound of formula (I) can be in the form of its E or Z isomer or of a mixture thereof, e.g. the invention comprises compositions of matter consisting of one or more compounds of formula (I), having the same chemical structure but differing by the configuration of the double bond. In particular, compound (I) can be in the form of a mixture consisting of isomers E and Z and wherein said isomers E represent at least 50% of the total mixture, or even at least 75% (i.e a mixture E/Z comprised between 75/25 and 100/0).

The terms "alkyl" "alkanediyl" are understood as comprising branched and linear alkyl and alkanediyl groups. The terms "cycloalkenyl" are understood as comprising 1, 2 or 3 olefinic double bonds, preferably 1 or 2 olefinic double bonds. The terms "cycloalkyl" and "cycloalkenyl" are understood as comprising a monocyclic or fused, spiro and/or bridged bicyclic or tricyclic cycloalkyl and cycloalkenyl, groups, preferably monocyclic cycloalkyl and cycloalkenyl groups.

For the sake of clarity, by the expression "one or two groups among $R^3$, $R^4$, $R^5$, $R^6$, $R^7$ and $R^8$ are taken together and form a $C_{3-8}$ cycloalkyl or $C_{5-8}$ cycloalkenyl group a . . . ", it is meant that the carbon atom(s) to which both groups are bonded is/are included into the $C_{5-8}$ cycloalkyl or $C_{5-8}$ cycloalkenyl group.

According to any embodiment of the invention, $R^1$ and $R^2$, independently from each other, represent a hydrogen atom or a methyl group. Particularly, $R^1$ may be a hydrogen atom or a methyl group and $R^2$ may be a hydrogen atom. Even more particularly, $R^1$ and $R^2$ may be a hydrogen atom. In other words, compound of formula (II) is a carbaldehyde of formula (II')

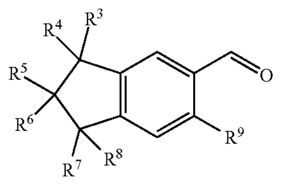

in the form of any one of their stereoisomers or a mixture thereof, and wherein $R^3$, $R^4$, $R^5$, $R^6$, $R^7$, $R^8$ and $R^9$ have the same meaning as defined above;

the acetal is an acetal of formula (III')

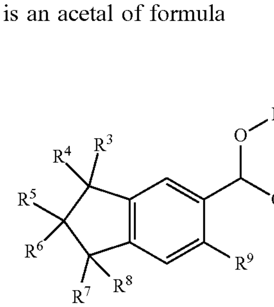

in the form of any one of their stereoisomers or a mixture thereof, and wherein $R^3$, $R^4$, $R^5$, $R^6$, $R^7$, $R^8$ and $R^9$ have the same meaning as defined above; $R^a$ and $R^b$, independently from each other, represent a $C_{1-4}$ alkyl group or $R^a$ and $R^b$, when taken together, represent a $C_{2-5}$ alkanediyl group;

the compound of formula $CHR^1{=}CH{-}OR^c$ is of formula $CH_2{=}CH{-}OR^c$; wherein $R^c$ represents a $C_{1-4}$ alkyl group; and the compound of formula (IV) is of formula (IV')

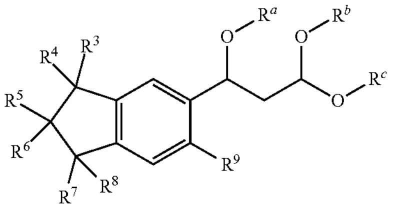

in the form of any one of their stereoisomers or a mixture thereof, and wherein $R^3$, $R^4$, $R^5$, $R^6$, $R^7$, $R^8$, $R^9$, $R^a$, $R^b$ and $R^c$ have the same meaning as defined above.

According to any embodiment of the invention, $R^3$, $R^4$, $R^5$, $R^6$, $R^7$ and $R^8$, independently from each other, represent a hydrogen atom or a $C_{1-3}$ alkyl group. Particularly, at least one group among, $R^3$, $R^4$, $R^5$, $R^6$, $R^7$ and $R^8$ may be a $C_{1-3}$ alkyl group and the others may be, independently from each other, a hydrogen atom or a $C_{1-3}$ alkyl. Particularly, at least three groups among $R^3$, $R^4$, $R^5$, $R^6$, $R^7$ and $R^8$ may be a hydrogen atom, the others, may be, independently from each other, a hydrogen atom or a $C_{1-3}$ alkyl group. Particularly, four groups among $R^3$, $R^4$, $R^5$, $R^6$, $R^7$ and $R^8$ may be a hydrogen atom, the others, may be, independently from each other, a hydrogen atom or a $C_{1-3}$ alkyl group. Particularly, one, two, three or four groups among $R^3$, $R^4$, $R^5$, $R^6$, $R^7$ and $R^8$ may be a $C_{1-3}$ alkyl group and the others may be a hydrogen atom. Even more particularly, one or two groups among $R^3$, $R^4$, $R^5$, $R^6$, $R^7$ and $R^8$ may be a $C_{1-3}$ alkyl group and the others may be a hydrogen atom.

According to any embodiment of the invention, $R^a$ and $R^b$, independently from each other, may be a $C_{1-3}$ alkyl group. Particularly, $R^a$ and $R^b$, independently from each other, may be a methyl or ethyl group. Even more particularly, $R^a$ and $R^b$, independently from each other, may be a methyl group.

According to any embodiment of the invention, $R^c$ may be a $C_{1-3}$ alkyl group. Particularly, $R^c$ may be a methyl or ethyl group. Even more particularly, $R^c$ is an ethyl group.

According to any embodiment of the invention, $R^9$ may be a hydrogen atom.

Non limiting examples of compound of formula (II) may include 3,3-dimethyl-2,3-dihydro-1H-indene-5-carbaldehyde, 1,1-dimethyl-2,3-dihydro-1H-indene-5-carbaldehyde, 1,3-dimethyl-2,3-dihydro-1H-indene-5-carbaldehyde, 2,2-dimethyl-2,3-dihydro-1H-indene-5-carbaldehyde 3-methyl-2,3-dihydro-1H-indene-5-carbaldehyde, 1-methyl-2,3-dihydro-1H-indene-5-carbaldehyde, 2-methyl-2,3-dihydro-1H-indene-5-carbaldehyde, 3,6-dimethyl-2,3-dihydro-1H-indene-5-carbaldehyde, 1,6-dimethyl-2,3-dihydro-1H-indene-5-carbaldehyde, 3-ethyl-2,3-dihydro-1H-indene-5-carbaldehyde, 1-ethyl-2,3-dihydro-1H-indene-5-carbaldehyde, 2-ethyl-2,3-dihydro-1H-indene-5-carbaldehyde, 3-iso-propyl-2,3-dihydro-1H-indene-5-carbaldehyde, 1-iso-propyl-2,3-dihydro-1H-indene-5-carbaldehyde, 2-iso-propyl-2,3-dihydro-1H-indene-5-carbaldehyde, 3-n-propyl-2,3-dihydro-1H-indene-5-carbaldehyde, 1-n-propyl-2,3-dihydro-1H-indene-5-carbaldehyde, 2-n-propyl-2,3-dihydro-1H-indene-5-carbaldehyde, 3-ethyl-3-methyl-2,3-dihydro-1H-indene-5-carbaldehyde, 1-ethyl-1-methyl-2,3-dihydro-1H-indene-5-carbaldehyde, 2,2,3,3-tetramethyl-2,3-dihydro-1H-indene-5-carbaldehyde or 1,1,2,2-tetramethyl-2,3-dihydro-1H-indene-5-carbaldehyde.

Non limiting examples of compound of formula (I) may include 3,3-dimethyl-2,3-dihydro-1H-indene-5-acrylaldehyde, 1,1-dimethyl-2,3-dihydro-1H-indene-5-acrylaldehyde, 1,3-dimethyl-2,3-dihydro-1H-indene-5-acrylaldehyde, 2,2-dimethyl-2,3-dihydro-1H-indene-5-acrylaldehyde 3-methyl-2,3-dihydro-1H-indene-5-acrylaldehyde, 1-methyl-2,3-dihydro-1H-indene-5-acrylaldehyde, 2-methyl-2,3-dihydro-1H-indene-5-acrylaldehyde, 3,6-dimethyl-2,3-dihydro-1H-indene-5-acrylaldehyde, 1,6-dimethyl-2,3-dihydro-1H-indene-5-acrylaldehyde, 3-ethyl-2,3-dihydro-1H-indene-5-acrylaldehyde, 1-ethyl-2,3-dihydro-1H-indene-5-acrylaldehyde, 2-ethyl-2,3-dihydro-1H-indene-5-acrylaldehyde, 3-iso-propyl-2,3-dihydro-1H-indene-5-acrylaldehyde, 1-iso-propyl-2,3-dihydro-1H-indene-5-acrylaldehyde, 2-iso-propyl-2,3-dihydro-1H-indene-5-acrylaldehyde, 3-n-propyl-2,3-dihydro-1H-indene-5-acrylaldehyde, 1-n-propyl-2,3-dihydro-1H-indene-5-acrylaldehyde, 2-n-propyl-2,3-dihydro-1H-indene-5-acrylaldehyde, 1-ethyl-3-methyl-2,3-dihydro-1H-indene-5-acrylaldehyde, 1-ethyl-1-methyl-2,3-dihydro-1H-indene-5-acrylaldehyde, 2,2,3,3-tetramethyl-2,3-dihydro-1H-indene-5-acrylaldehyde or 1,1,2,2-tetramethyl-2,3-dihydro-1H-indene-5-acrylaldehyde.

According to any embodiment of the invention, the compound of formula (II) may be in a form of a mixture of regioisomers. Compound of formula (I), obtained through the invention's process starting from compound of formula (II) being in a form of a mixture of regioisomers, will be in the formed of a mixture of regioisomers, The ratio between each isomers is maintained through the invention's process.

For the sake of clarity, by the expression "in a form of a mixture of regioisomers", or the similar, it is meant the normal meaning understood by a person skilled in the art, i.e. that compound of formula (II) may be in a form of a mixture comprising at least two different regioisomers wherein the carbonyl functional group is, for one regioisomer, in ortho, meta or para position and, for the second regioisomer, in another position than the other regioisomers; e.g. compound of formula (II) may be in a form of a mixture comprising 3,3-dimethyl-2,3-dihydro-1H-indene-5-carbaldehyde and 1,1-dimethyl-2,3-dihydro-1H-indene-5-carbaldehyde. The compound of formula (II) may be in a form of a mixture comprising at most 3 different regioisomers. In other words, the compound of formula (II) may be in a form of a mixture comprising compounds with the same chemical structure but differing only by the position of the carbonyl functional group or acrylaldehyde group for compound of formula (I). The regioisomers differ only by the position of the substituent(s) on the aromatic ring of compounds of formula (I), (II), (III), (IV) and (V):

According to any embodiments of the invention, the conversion of the compound of formula (II) into acetal of formula (III) may be carried out under normal condition known by the person skilled in the art, i.e. in the presence of an acid such as Bronsted acid or a Lewis acid compatible with alcohols, such as Lanthanide triflates, and a reagent selected from the group consisting of $C_{1-4}$ trialkyl orthoformate, $C_{1-4}$ alcohol and $C_{2-5}$ diol. The conversion of benzaldehyde or benzaldehyde derivatives into the corresponding acetal is well known and has been largely reported in the prior art. So, the person skilled in the art will be able to set up the best conditions in order to convert compound of formula (II) into compound of formula (III). As non-limiting example, the step a) may be performed under the conditions reported in *Green Chemistry,* 2013, 15(10), 2740-2746*; Synthesis,* 2009, (23), 4082-4086*; Synlett,* 2002, (2), 319-321*; Tetrahedron Letters,* 2004, 45(26), 5135-5138*; Current Organocatalysis,* 2018, 5(3), 196-200 or *Tetrahedron Letters,* 2004, 45(44), 8141-8144. According to a particular embodiment of the invention, the acid used in step a) may have a pKa below 3. Specific and non-limiting examples of Bronsted acid may be selected from the group consisting of para toluene sulfonic acid, methane sulfonic acid, camphor sulfonic acid, methane disulfonic acid, methane trisulfonic acid, 2,4 dinitrobenzene sulfonic acid. Particularly, the Bronsted acid may be para-toluene sulfonic acid. Specific and non-limiting examples of Lewis acid compatible with alcohols may be selected from the group consisting of metal triflates such as $Al(OTf)_3$, Lanthanide triflates such as $Sc(OTf)_3$, $Bi(OTf_3$, metal tetrafluoroborates such as $Zn(BF_4)_2$, and zinc halides such as $ZnCl_2$, $ZnBr_2$. Specific and non-limiting examples of $C_{1-4}$ trialkyl orthoformate, $C_{1-4}$ alcohol or $C_{2-5}$ diol may be selected from the group consisting of methanol, ethanol, ethylene glycol, trimethyl orthoformate, triethylorthoformate.

The $C_{1-4}$ trialkyl orthoformate, $C_{1-4}$ alcohol or $C_{2-5}$ diol can be added into the reaction medium of the invention's process in a large range of concentrations. As non-limiting examples, one can cite as $C_{1-4}$ trialkyl orthoformate or $C_{2-5}$ diol concentration values those ranging from about 1 to about 2 equivalents, relative to the amount of the of substrate, preferably from 1 to about 1.5 equivalents, relative to the amount of the of substrate. As non-limiting examples, one can cite as $C_{1-4}$ alcohol concentration values those ranging from about 2 to about 15 equivalents, relative to the amount of the of substrate, preferably from 3 to about 5 equivalents, relative to the amount of the of substrate The optimum concentration of the $C_{1-4}$ trialkyl orthoformate, $C_{1-4}$ alcohol or $C_{2-5}$ diol will depend, as the person skilled in the art knows, on the nature of the latter, on the nature of the substrate, on the reaction temperature as well as on the desired time of reaction.

The Bronsted acid can be added into the reaction medium of the invention's process in a large range of concentrations. As non-limiting examples, one can cite as acid concentration values those ranging from about 0.1 to about 5 mol %, relative to the amount of the of substrate, preferably from 0.5 to about 3 mol %, relative to the amount of the of substrate The optimum concentration of the Bronsted acid will depend, as the person skilled in the art knows, on the nature of the latter, on the nature of the substrate, on the nature of the $C_{1-4}$ trialkyl orthoformate, $C_{1-4}$ alcohol or $C_{2-5}$ diol, on the reaction temperature as well as on the desired time of reaction.

According to any one of the invention's embodiments, the invention's process to form compound of formula (III) is carried out at a temperature comprised between 20° C. and 55° C. In particular, the temperature is in the range between 20° C. and 30° C. Of course, a person skilled in the art is also able to select the preferred temperature as a function of the melting and boiling point of the starting and final products as well as the desired time of reaction or conversion.

The acetal formation can be carried out in the presence or absence of a solvent. When a solvent is required or used for practical reasons, then any solvent current in such reaction type can be used for the purposes of the invention. Non-limiting examples include $C_{6-12}$ aromatic solvents such as toluene, 1,3-diisopropylbenzene, cumene or pseudocumene, or mixtures thereof, alcoholic solvent such as methanol, ethanol, or mixtures thereof, hydrocarbon solvents such as cyclohexane or heptane, ethyl acetate or ethereal solvents such as methyl tetrahydrofuran, tetrahydrofuran or mixtures thereof. The choice of the solvent is function of the nature of the substrate and/or catalyst and the person skilled in the art is well able to select the solvent most suitable in each case to optimize the reaction.

According to any embodiments of the invention, the treatment of the acetal of formula (III) may be carried with a compound of formula $CHR^1{=}CH{-}OR^c$; wherein $R^c$ represents a $C_{1-3}$ alkyl group and $R^1$ has the same meaning as defined above. Particularly, $R^1$ may be a hydrogen atom and $R^c$ may represent a $C_{1-2}$ alkyl group. Even more particularly $R^c$ may represent an ethyl group. Specific and non-limiting examples of acid used in step b) may be selected from the group consisting of Boron trifluoride complexes, such as $BF_3{\cdot}OEt_2$, $BF_3{\cdot}OBu_2$, $BF_3{\cdot}(AcOH)_2$ or $BF_3{\cdot}MeCN$, anhydrous zinc chloride, para toluene sulfonic acid. Particularly, the acid use is step b) is a Lewis acid.

The compound of formula $CHR^1{=}CH{-}OR^c$ can be added into the reaction medium of the invention's process in a large range of concentrations. As non-limiting examples, one can cite as enol ether concentration values those ranging from about 1 to about 5 equivalents, relative to the amount of the substrate, preferably from 1.1 to about 1.2 equivalents, relative to the amount of the of substrate The optimum concentration of the compound of formula $CHR^1{=}CH{-}OR^c$ will depend, as the person skilled in the art knows, on the nature of the latter, on the nature of the substrate, on the reaction temperature as well as on the desired time of reaction.

The acid used in step b) can be added into the reaction medium of the invention's process in a large range of concentrations. As non-limiting examples, one can cite as acid concentration values those ranging from about 0.001 mol % to about 10 mol %, relative to the amount of the of substrate, preferably from 0.01 mol % to about 5 mol %, relative to the amount of the of substrate The optimum concentration of the acid used in step b) will depend, as the person skilled in the art knows, on the nature of the latter, on the nature of the substrate, on the reaction temperature as well as on the desired time of reaction.

According to any one of the invention's embodiments, the invention's process to form compound of formula (IV) is carried out at a temperature comprised between 10° C. and 100° C. In particular, the temperature is in the range between 15° C. and 25° C. Of course, a person skilled in the art is also able to select the preferred temperature as a function of the melting and boiling point of the starting and final products as well as the desired time of reaction or conversion.

The step b) of the invention's process can be carried out in the presence or absence of a solvent. When a solvent is required or used for practical reasons, then any solvent current in such reaction type can be used for the purposes of the invention. Non-limiting examples include $C_{6-12}$ aromatic solvents such as toluene, 1,3-diisopropylbenzene, cumene or pseudocumene, or mixtures thereof, ethyl acetate or ethereal solvents such as methyl tetrahydrofuran, tetrahydrofuran or mixtures thereof or chlorinated solvents such dichloromethane, dichloroethane or a mixture thereof. The choice of the solvent is function of the nature of the substrate and/or catalyst and the person skilled in the art is well able to select the solvent most suitable in each case to optimize the reaction. Particularly, the step b) may be carried out in absence of solvent.

According to any one of the invention's embodiments, steps a) and b) of the invention's process are done in one pot with an acid such as boron trifluoride acetic acid complex, para toluene sulfonic acid, or camphor sulfonic acid.

According to any one of the invention's embodiments, the acid used in step c) may be selected from the group consisting of acetic acid, aqueous acetic acid, propionic acid, aqueous sulfuric acid, sulfuric acid, aqueous hydrochloric acid. Particularly, the acid used in step c) may be acetic acid.

The acid used in step c) can be added into the reaction medium of the invention's process in a large range of concentrations. As non-limiting examples, one can cite as acid concentration values those ranging from about 1 to about 10 equivalents, relative to the amount of the of substrate, preferably from 3 to about 8 equivalents, relative to the amount of the of substrate The optimum concentration of the acid used in step c) will depend, as the person skilled in the art knows, on the nature of the latter, on the nature of the substrate, on the reaction temperature as well as on the desired time of reaction.

According to any one of the invention's embodiments, the invention's process to form compound of formula (I) is carried out at a temperature comprised between 25° C. and 150° C. In particular, the temperature is in the range between 90° C. and 120° C. Of course, a person skilled in the art is also able to select the preferred temperature as a function of the melting and boiling point of the starting and final products as well as the desired time of reaction or conversion.

The step c) can be carried out in the presence or absence of a solvent. When a solvent is required or used for practical reasons, then any solvent current in such reaction type can be used for the purposes of the invention. Non-limiting examples include $C_{6-12}$ aromatic solvents such as toluene, 1,3-diisopropylbenzene, cumene or pseudocumene, or mixtures thereof, alcoholic solvent such as methanol, ethanol, or mixtures thereof, hydrocarbon solvents such as but not limited to, cyclohexane or heptane, ethyl acetate or ethereal solvents such as methyl tetrahydrofuran, tetrahydrofuran, 1,4-dioxane or mixtures thereof. The choice of the solvent is function of the nature of the substrate and/or catalyst and the person skilled in the art is well able to select the solvent most suitable in each case to optimize the reaction.

According to any embodiment of the invention, the invention's process may be carried out in one pot; i.e. step a) to c) may be performed without isolation step of any intermediate.

According to any embodiment of the invention, the invention's process for the preparation of compound of formula (I) may be carried out under batch or continuous conditions.

According to any embodiment of the invention, the compound of formula (I) may be hydrogenated into a compound of formula (V)

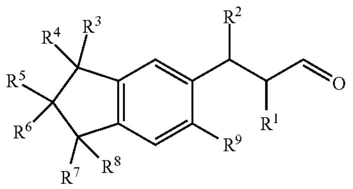

in the form of any one of their stereoisomers or a mixture thereof, and wherein $R^1$, $R^2$, $R^3$, $R^4$, $R^5$, $R^6$, $R^7$, $R^8$ and $R^9$ have the same meaning as defined above. The person skilled in the art is well aware of the conditions to apply in order to obtain compound of formula (V).

The compound of formula (III), (IV) and (V) are, generally, novel compounds and present a number of advantages as explained above and shown in the Examples. Therefore, another object of the present invention is a compound of formula (III)

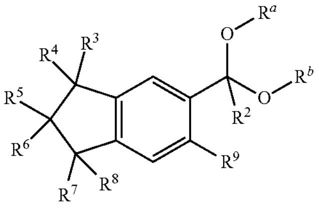

in the form of any one of their stereoisomers or a mixture thereof, and wherein $R^2$ represents a hydrogen atom or a $C_{1-2}$ alkyl group $R^3$, $R^4$, $R^5$, $R^6$, $R^7$ and $R^8$, independently from each other, represent a hydrogen atom or a $C_{1-4}$ alkyl group; or two groups among $R^3$, $R^4$, $R^5$, $R^6$, $R^7$ and $R^8$ are taken together and form a $C_{3-8}$ cycloalkyl or $C_{5-8}$ cycloalkenyl group and the others groups have the same meaning as defined above; $R^9$ represents a hydrogen atom or a methyl group; $R^a$ and $R^b$, independently from each other, represent a $C_{1-4}$ alkyl group or $R^a$ and $R^b$, when taken together, represent a $C_{2-5}$ alkanediyl group; provided that when $R^a$ and $R^b$ are ethyl groups, then $R^3$, $R^4$, $R^5$, $R^6$, $R^7$ and $R^8$ are not hydrogen atoms and when $R^a$ and $R^b$ are methyl or ethyl groups or $R^a$ and $R^b$ are taken together and represent a 1,2-ethandiyl group, then $R^3$, $R^4$, $R^5$, $R^7$ and $R^8$ being methyl groups and $R^6$ being a hydrogen atom or $R^3$, $R^4$ and $R^8$ being methyl groups, $R^7$ being a ethyl group and $R^5$ and $R^6$ being hydrogen atoms are excluded.

Another object of the present invention is compound of formula

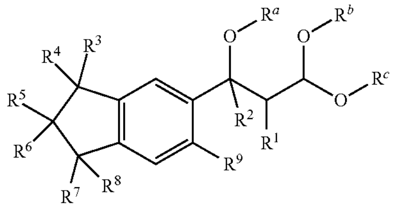

(IV)

in the form of any one of their stereoisomers or a mixture thereof, and wherein $R^1$ and $R^2$, independently from each other, represent a hydrogen atom or a $C_{1-2}$ alkyl group $R^3$, $R^4$, $R^5$, $R^6$, $R^7$ and $R^8$, independently from each other, represent a hydrogen atom or a $C_{1-4}$ alkyl group; or two groups among $R^3$, $R^4$, $R^5$, $R^6$, $R^7$ and $R^8$ are taken together and form a $C_{3-8}$ cycloalkyl or $C_{5-8}$ cycloalkenyl group and the others groups have the same meaning as defined above; $R^9$ represents a hydrogen atom or a methyl group; $R^a$ and $R^b$, independently from each other, represent a $C_{1-4}$ alkyl group or $R^a$ and $R^b$, when taken together, represent a $C_{2-5}$ alkanediyl group; $R^c$ represents a $C_{1-4}$ alkyl group.

A further object of the present invention is compound of formula (V) as defined above, provided that when $R^9$ is a hydrogen atom, at least one group among $R^3$, $R^4$, $R^5$, $R^6$, $R^7$ and $R^8$, is a $C_{1-4}$ alkyl group; or when $R^9$ is a hydrogen atom and $R^5$ is a methyl or a n-propyl group, at least one group among $R^1$, $R^3$, $R^4$, $R^6$, $R^7$ and $R^8$, is not a hydrogen atom; or 3-(3-methyl-2,3-dihydro-1H-inden-5-yl)propanal, 3-(3-methyl-2,3-dihydro-1H-inden-5-yl)butanal, 3-(1,1-dimethyl-2,3-dihydro-1H-inden-5-yl)propanal, 3-(1,1-dimethyl-2,3-dihydro-1H-inden-5-yl)-2-methylpropanal, 3-(3,3-dimethyl-2,3-dihydro-1H-inden-5-yl)propanal, 3-(3,3-dimethyl-2,3-dihydro-1H-inden-5-yl)-2-methylpropanal or 3-(1,1,6-trimethyl-2,3-dihydro-1H-inden-5-yl)propanal are excluded.

Typical manners to execute the invention's process are reported herein below in the examples.

EXAMPLES

The invention will now be described in further detail by way of the following examples, wherein the abbreviations have the usual meaning in the art, the temperatures are indicated in degrees centigrade (° C.). NMR spectra were acquired using either a Bruker Avance II Ultrashield 400 plus operating at 400 MHz, ($^1$H) and 100 MHz ($^{13}$C) or a Bruker Avance III 500 operating at 500 MHz ($^1$H) and 125 MHz ($^{13}$C) or a Bruker Avance III 600 cryoprobe operating at 600 MHz ($^1$H) and 150 MHz ($^{13}$C). Spectra were internally referenced relative to tetramethyl silane 0.0 ppm. $^1$H NMR signal shifts are expressed in δ ppm, coupling constants (J) are expressed in Hz with the following multiplicities: s, singlet; d, doublet; t, triplet; q, quartet; m, multiplet; b, broad (indicating unresolved couplings) and were interpreted using Bruker Topspin software. $^{13}$C NMR data are expressed in chemical shift δ ppm and hybridization from DEPT 90 and DEPT 135 experiments, C, quaternary; CH, methine; $CH_2$, methylene; $CH_3$, methyl.

Example 1

Preparation of a mixture comprising 3-(3,3-dimethyl-2,3-dihydro-1H-inden-5-yl)acrylaldehyde and 3-(1,1-dimethyl-2,3-dihydro-1H-inden-5-yl)acrylaldehyde following the invention's process a) Step a): preparation of a mixture comprising 6-(diethoxymethyl)-1,1-dimethyl-2,3-dihydro-1H-indene and 6-(diethoxymethyl)-3,3-dimethyl-2,3-dihydro-1H-indene In a three-neck flask, a mixture of 3,3-dimethyl-2,3-dihydro-1H-indene-5-carbaldehyde and 1,1-dimethyl-2,3-dihydro-1H-indene-5-carbaldehyde (15 g, 1 eq), ethanol (15 mL) and triethyl orthoformate (19.1 g, 1.5 eq) were added at rt. p-TSA (0.13 g, 0.008 eq) was dissolved into 5 mL ethanol and was added slowly. The reaction mixture was heated to 50-55° C. and the progress of the reaction was monitored by GC. After completion of the reaction, sodium ethoxide (21%) (0.141 g, 0.02 eq) was added and it was cooled to rt. The solvents were removed at reduced pressure to give crude mixture of 6-(diethoxymethyl)-1,1-dimethyl-2,3-dihydro-1H-indene and 6-(diethoxymethyl)-3,3-dimethyl-2,3-dihydro-1H-indene. The purification of crude products by flash distillation gave (20 g, 92%) pure diethylacetals mixture comprising 6-(diethoxymethyl)-1,1-dimethyl-2,3-dihydro-1H-indene and 6-(diethoxymethyl)-3,3-dimethyl-2,3-dihydro-1H-indene in the same ratio than the starting material.

$^1$H ($CDCl_3$, 500 MHz): δ 7.37-7.06 (m, 3H), 5.46, 5.44 (each s, 1H), 3.69-3.48 (m, 4H), 2.91-2.83 (m, 2H), 1.92, 1.91 (each t, J 7.3, 2H), 1.26-1.21 (m, 15H) ppm.

$^{13}$C ($CDCl_3$, 125 MHz) δ 152.7, 152.6, 142.9, 142.8, 137.4, 137.2, 124.9, 127.8, 122.6, 121.6, 120.2, 102.1 (d), 61.3, 61.2, 43.9, 43.7, 41.6, 41.5, 30.0, 29.8, 28.6, 15.2 ppm.

b) Step b): preparation of a mixture comprising 1,1-dimethyl-6-(1,3,3-triethoxypropyl)-2,3-dihydro-1H-indene and 3,3-dimethyl-6-(1,3,3-triethoxypropyl)-2,3-dihydro-1H-indene Under an atmosphere of nitrogen anhydrous zinc chloride (0.03 eq, 172 mg) was added to a stirred solution of diethylacetals obtained in step a) (9.3 g, 42.3 mmol) in dichloromethane (50 mL) at 20° C. (water bath). Ethyl vinyl ether (3.2 g, 44 mmol) was then added slowly dropwise over 20 minutes using the water bath to maintain the reaction temperature between 15-20° C. The reaction mixture was stirred for a further 90 minutes at ambient temperature then tripotassium citrate solution (1.0 M) was added and the mixture stirred for a further 60 minutes at ambient temperature. The organic phase was re extracted with dichloromethane, then the combined organic phase was washed with water, sodium bicarbonate solution, brine then dried over $MgSO_4$ and filtered. The solvents were removed in vacuo and then the residue further purified by Kügelrohr distillation (110-115° C., 0.1 mbar) to give 9.8 g, of a mixture comprising 1,1-dimethyl-6-(1,3,3-triethoxypropyl)-2,3-dihydro-1H-indene and 3,3-dimethyl-6-(1,3,3-triethoxypropyl)-2,3-dihydro-1H-indene which was used without further purification in the next step.

c) Step c): preparation of a mixture comprising 3-(3,3-dimethyl-2,3-dihydro-1H-inden-5-yl)acrylaldehyde and 3-(1,1-dimethyl-2,3-dihydro-1H-inden-5-yl)acrylaldehyde A solution of the triethylacetals obtained in step b) (9.8 g, 33.5 mmol) and 1,4 dioxane (18 g) and 10% $H_2SO_4$ (2.0 g)

was heated at 100° C. for 12 hours then cooled and the mixture was partitioned between diethyl ether and water. The aqueous phase was re extracted with diethyl ether, then the combined organic phase was washed with water, saturated sodium bicarbonate, brine, dried over anhydrous sodium sulfate, filtered and the solvents removed in vacuo to yield the mixture comprising 3-(3,3-dimethyl-2,3-dihydro-1H-inden-5-yl)acrylaldehyde and 3-(1,1-dimethyl-2,3-dihydro-1H-inden-5-yl)acrylaldehyde, 6.6 g. Further purification by Kügelrohr distillation (110-115° C., 0.5 mbar) gave a mixture comprising 3-(3,3-dimethyl-2,3-dihydro-1H-inden-5-yl)acrylaldehyde and 3-(1,1-dimethyl-2,3-dihydro-1H-inden-5-yl)acrylaldehyde in the same ratio than the starting material, 5.8 g.

$^1$H ($CDCl_3$, 500 MHz): δ 9.68 (d, J 3.2, 1H), 9.66 (d, J 3.2, 1H), 9.49 (d, 7.1, 1H), 7.44 (d, J 7.1, 1H), 7.41-7.21 (m, 3H), 7.18 (d, J 7.9, 1H), 6.74-6.64 (m, 2H), 2.92 (t, J 7.3, 2H), 1.95 (t, J 7.3, 2H), 1.28 (s, 3H), 1.27 (s, 3H) ppm.

$^{13}$C ($CDCl_3$, 125 MHz) δ 193.8 (d), 156.8, 153.7, 153.6, 153.5, 147.2, 143.9, 132.6, 132.2, 127.6, 127.5, 127.5, 127.3, 125.2, 124.4, 122.6, 121.9, 44.1, 43.8, 41.3, 41.2, 30.2, 29.7, 28.5, 28.3 ppm.

Example 2

Preparation of a mixture comprising 3-(3,3-dimethyl-2,3-dihydro-1H-inden-5-yl)acrylaldehyde and 3-(1,1-dimethyl-2,3-dihydro-1H-inden-5-yl)acrylaldehyde following the one pot invention's process pTSA (0.8 g, 1 mol %) was added in one portion to a solution of 3,3-dimethyl-2,3-dihydro-1H-indene-5-carbaldehyde and 1,1-dimethyl-2,3-dihydro-1H-indene-5-carbaldehyde (82.1 g, 462 mmol) and triethyl orthoformate (96.2 g, 650 mmol) and the mixture heated at 90° C. for 60 minutes then cooled to 60° C. and zinc chloride (1.9 g, 0.03 eq) was added and then butyl vinyl ether (55.0 g, 550 mmol) slowly dropwise over 60 minutes. The mixture was stirred at 60° C. for 5 hours then at 20° C. overnight. Hydroquinone (2.0 g) was added followed by isopropanol (160 g) and 10% sulfuric acid (80 g over 15 minutes) and the reaction mixture heated at 90° C. for 6 hours and the volatiles collected. The solution was cooled, diluted with toluene (200 g) and washed with water (2×100 g), then saturated sodium bicarbonate solution (120 g) dried over $MgSO_4$, filtered and the solvents removed in vacuo to give the crude mixture comprising 3-(3,3-dimethyl-2,3-dihydro-1H-inden-5-yl)acrylaldehyde and 3-(1,1-dimethyl-2,3-dihydro-1H-inden-5-yl) acrylaldehyde, 113.7 g. Further distillation, 100-120° C. at 0.5 mbar gave the pure mixture comprising 3-(3,3-dimethyl-2,3-dihydro-1H-inden-5-yl)acrylaldehyde and 3-(1,1-dimethyl-2,3-dihydro-1H-inden-5-yl)acrylaldehyde in the same ratio than the starting material, 65.5 g, (71% overall yield).

Example 3

Hydrogenation of a mixture comprising 3-(3,3-dimethyl-2,3-dihydro-1H-inden-5-yl)acrylaldehyde and 3-(1,1-dimethyl-2,3-dihydro-1H-inden-5-yl)acrylaldehyde A suspension of palladized charcoal (5% Pd/C, 0.2 g), the mixture obtained in example 1 (5.8 g, 29 mmol), potassium acetate (60 mg) in ethyl acetate (20 mL) was evacuated in vacuo and then purged with hydrogen gas (3×) then stirred under an atmosphere of hydrogen for 12 hours then filtered. The solvent was removed in vacuo and the residue (6.2 g) was purified by flash chromatography (220 g cartridge, heptane:MTBE 99:1-3:97 as eluant) to separate the small amount of alcohol formed (ca. 20%) and gave the desired aldehyde as a mixture of regioisomers (same ratio than the starting material), 4.0 g which was further purified by Kügelrohr distillation (105-110° C., 1.0 mbar) to give the pure aldehyde 3.2 g, 54% as a mixture of regioisomers (same ratio than the starting material).

$^1$H ($CDCl_3$, 500 MHz): δ 9.82-9.80 (m, 1H), 7.12-6.94 (m, 3H), 2.93 (q, J 7.8, 2H), 2.87-2.82 (m, 2H9, 2.78-2.73 (m, 2H), 1.91 (t, J 7.2, 2H), 1.24 (s, 3H), 1.23 (s, 3H) ppm.

$^{13}$C ($CDCl_3$, 125 MHz) δ201.9, 201.9 (d), 153.1, 150.7 (s), 143.3, 140.9 (s), 138.4, 138.2 (s), 126.4, 126.2 (d), 124.5, 124.4 (d), 122.0, 121.9 (d), 45.7, 45.5 (t), 43.9, 43.6 (s), 41.6, 41.5 (t), 29.9, 29.6 (t), 28.6, 28.5 (q), 28.6 (q), 28.2, 28.0 (t) ppm.

The invention claimed is:

1. A process for the preparation of a compound of formula (I)

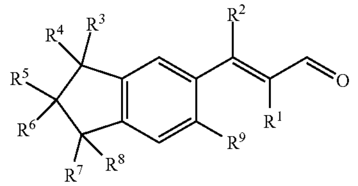

in the form of any one of their stereoisomers or a mixture thereof, and wherein $R^1$ and $R^2$, independently from each other, represent a hydrogen atom or a $C_{1-2}$ alkyl group; $R^9$ represents a hydrogen atom or a methyl group; $R^3$, $R^4$, $R^5$, $R^6$, $R^7$ and $R^8$, independently from each other, represent a hydrogen atom or a $C_{1-4}$ alkyl group; or two groups among $R^3$, $R^4$, $R^5$, $R^6$, $R^7$ and $R^8$ are taken together and form a $C_{3-8}$ cycloalkyl or $C_{5-8}$ cycloalkenyl group and the other groups have the same meaning as defined above;

comprising the steps of a) converting a compound of formula (II)

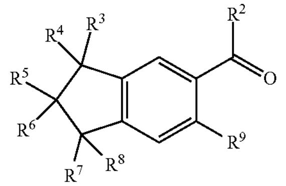

in the form of any one of their stereoisomers or a mixture thereof, and wherein $R^2$, $R^3$, $R^4$, $R^5$, $R^6$, $R^7$, $R^8$ and $R^9$ have the same meaning as defined above;

into an acetal of formula (III)

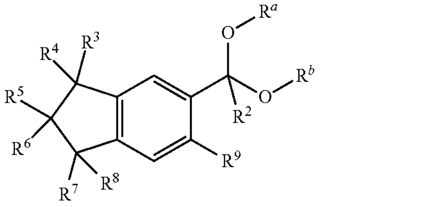

in the form of any one of their stereoisomers or a mixture thereof, and wherein $R^2$, $R^3$, $R^4$, $R^5$, $R^6$, $R^7$, $R^8$ and $R^9$ have the same meaning as defined above; $R^a$ and $R^b$, independently from each other, represent a $C_{1-4}$ alkyl group or $R^a$ and $R^b$, when taken together, represent a $C_{2-5}$ alkanediyl group;

b) treating the acetal obtained in step a) with an acid and a compound of formula $CHR^1{=}CH{-}OR^c$; wherein $R^c$ represents a $C_{1-4}$ alkyl group and $R^1$ has the same meaning as defined above; to obtain a compound of formula (IV)

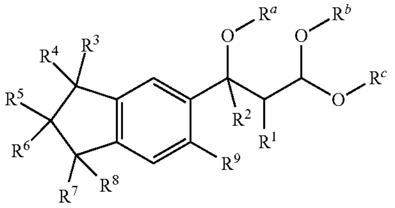

in the form of any one of their stereoisomers or a mixture thereof, and wherein $R^1$, $R^2$, $R^3$, $R^4$, $R^5$, $R^6$, $R^7$, $R^8$, $R^9$, $R^a$, $R^b$ and $R^c$ have the same meaning as defined above; and c) treating the compound of formula (IV) with an acid to obtain a compound of formula (I).

2. The process according to claim 1, wherein $R^a$ and $R^b$, independently from each other, represent a $C_{1-3}$ alkyl group.

3. The process according to claim 1, wherein $R^a$ and $R^b$, independently from each other, represent a methyl group.

4. The process according to claim 1, wherein Reis a methyl or ethyl group.

5. The process according to claim 1, wherein $R^c$ is an ethyl group.

6. The process according to claim 1, wherein $R^1$ and $R^2$, independently from each other, represent a hydrogen atom or a methyl group.

7. The process according to claim 1, wherein $R^3$, $R^4$, $R^5$, $R^6$, $R^7$ and $R^8$, independently from each other, represent a hydrogen atom or a $C_{1-3}$ alkyl group.

8. The process according to claim 1, wherein one or two groups among $R^3$, $R^4$, $R^5$, $R^6$, $R^7$ and $R^8$ represent a $C_{1-3}$ alkyl group and the others represent a hydrogen atom.

9. The process according to claim 1, wherein step a) is carried out in the presence of an acid and a reagent selected from the group consisting of $C_{1-4}$ trialkyl orthoformate, $C_{1-4}$ alcohol and $C_{2-5}$ diol.

10. The process according to claim 1, wherein the acid used in step b) is selected from the group consisting of boron trifluoride complexes, anhydrous zinc chloride, and para toluene sulfonic acid.

11. The process according to claim 1, wherein the acid used in step c) is selected from the group consisting of acetic acid, aqueous acetic acid, propionic acid, aqueous sulfuric acid, sulfuric acid and aqueous hydrochloric acid.

12. The process according to claim 6, wherein $R^1$ and $R^2$, independently from each other, represent a hydrogen atom.

13. The process according to claim 1, wherein $R^a$ and $R^b$, independently from each other, represent a methyl group, $R^c$ is an ethyl group, $R^1$ and $R^2$, independently from each other, represent a hydrogen atom; and $R^3$, $R^4$, $R^5$, $R^6$, $R^7$ and $R^8$, independently from each other, represent a hydrogen atom or a $C_{1-3}$ alkyl group.

14. The process according to claim 13, wherein one or two groups among $R^3$, $R^4$, $R^5$, R, $R^7$ and $R^8$ represent a $C_{1-3}$ alkyl group and the others represent a hydrogen atom.

15. The process according to claim 1, wherein:

step a) is carried out in the presence of an acid and a reagent selected from the group consisting of $C_{1-4}$ trialkyl orthoformate, $C_{1-4}$ alcohol and $C_{2-5}$ diol;

the acid used in step b) is selected from the group consisting of boron trifluoride complexes, anhydrous zinc chloride, and para toluene sulfonic acid; and the acid used in step c) is selected from the group consisting of acetic acid, aqueous acetic acid, propionic acid, aqueous sulfuric acid, sulfuric acid and aqueous hydrochloric acid.

16. A process for the preparation of a compound of formula V, comprising:

preparing a compound of formula (I) according to the process of claim 1; and hydrogenating the compound of formula (I) into a compound of formula (V)

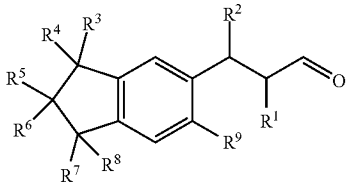

in the form of any one of their stereoisomers or a mixture thereof, and wherein $R^1$ and $R^2$, independently from each other, represent a hydrogen atom or a $C_{1-2}$ alkyl group; $R^9$ represents a hydrogen atom or a methyl group; $R^3$, $R^4$, $R^5$, $R^6$, $R^7$ and $R^8$, independently from each other, represent a hydrogen atom or a $C_{1-4}$ alkyl group; or two groups among $R^3$, $R^4$, $R^5$, $R^6$, $R^7$ and $R^8$ are taken together and form a $C_{3-8}$ cycloalkyl or $C_{5-8}$ cycloalkenyl group and the other groups have the same meaning as defined above.

* * * * *